(12) United States Patent
Serizawa et al.

(10) Patent No.: US 6,532,385 B2
(45) Date of Patent: Mar. 11, 2003

(54) LIVING BODY MEASURING APPARATUS WITH BUILT-IN WEIGHT METER

(75) Inventors: Takashi Serizawa, Tokyo (JP); Takeshi Iijima, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/776,719

(22) Filed: Feb. 6, 2001

(65) Prior Publication Data

US 2001/0014777 A1 Aug. 16, 2001

(30) Foreign Application Priority Data

Feb. 16, 2000 (JP) ........................................ 2000-037570

(51) Int. Cl.[7] ................................................. A61B 5/00
(52) U.S. Cl. ........................................ 600/547; 600/595
(58) Field of Search ................................. 600/546, 547, 600/585

(56) References Cited

U.S. PATENT DOCUMENTS

| | | | |
|---|---|---|---|
| 4,699,804 A | 10/1987 | Miyata et al. | |
| 5,415,176 A | 5/1995 | Sato et al. | |
| 6,088,615 A | * 7/2000 | Masuo | 600/547 |
| 6,208,890 B1 | * 3/2001 | Sarrazin et al. | 600/547 |
| 6,327,494 B1 | * 12/2001 | Sakai | 600/547 |

FOREIGN PATENT DOCUMENTS

| | | |
|---|---|---|
| DE | 19639095 | 3/1998 |
| JP | 09033327 | 2/1997 |
| JP | 10096706 | 4/1998 |

* cited by examiner

*Primary Examiner*—Max F. Hindenburg
(74) *Attorney, Agent, or Firm*—McDermott, Will & Emery

(57) ABSTRACT

Disclosed is a living body measuring apparatus with a built-in weight meter, comprising: a measuring platform; and electrodes, whereby said measuring platform being constructed in two-layered configuration having inner and outer boards, said electrodes being arranged on said outer board to measure a living body impedance, and said outer board of the measuring platform being formed from a transparent plate. Therefore a paper bearing the caution notice or the description of operation can be affixed to the lower surface of the outer board because they are still visible through the transparent outer board. This obviates the tendency for a person to be measured to inevitably tread the paper with his soles for measurement. Furthermore, if the person mounts the outer board with his feet as wetted after taking a bath, there is no possibility to wet the paper, thereby preventing the paper from peeling off.

9 Claims, 2 Drawing Sheets

LIVING BODY MEASURING APPARATUS WITH BUILT-IN WEIGHT METER

BACKGROUND OF THE INVENTION

1. Field of the Invention

The present invention relates to a living body measuring apparatus for measuring a living body impedance and for providing a body fat rate or other information useful for health care. More particularly the present invention relates to a living body measuring apparatus with a built-in weight meter that comprises a transparent measuring platform.

2. Description of the Prior Art

A body fat measuring apparatus with a built-in weight meter is currently available as one of the well-known living body measuring apparatus. Such body fat measuring apparatus comprises a measuring platform of two-layered configuration having inner and outer boards. In general the inner board of the measuring platform is formed from a rolled steal plate by a pressing process so that it has a shape like a cover for a box. The inner board has sufficient mechanical strength for transmitting a body weight without any permanent deformation when a person mounts the measuring platform.

The outer board of the measuring platform is generally formed from a colored plastic resin by an injection molding. The outer board also has a shape like a cover for a box and includes several ribs on the inner surface thereof The outer board is provided with electrodes formed by a pressing process for measuring a living body impedance. The outer board acts as an insulator between the electrodes. In order for a person to properly place his feet on the electrodes the outer board is provided with some indexing means such as convex portions for the reference for his heels or some index marks on a paper affixed thereon.

In addition a reflection type, low power consumption liquid crystal display is used for numerically or graphically indicating the measurement result.

The body fat measuring apparatus with the built-in weight meter, as described above, is very useful in that it can concurrently measure the body weight required for deriving the body fat rate.

However, in the body fat measuring apparatus, as above, it is common practice that a paper bearing an important information such as the caution notice or the description for operation is affixed either on the bottom surface of the apparatus or on the upper surface of the outer board of the measuring platform. Therefore it is necessary to turn the apparatus upside down to read such important information on the paper, if it is affixed on the bottom surface of the apparatus. On the other hand, if such paper is affixed on the upper surface of the outer board, it may possible that the paper becomes peeled off because it is repeatedly treaded with the feet of a person, and especially with the feet of a person as wetted after taking a bath.

In addition, when a person to be measured mount the outer board of the measuring platform, it is necessary to see the index marks on the outer board to correctly stand on the electrodes. However, if the person is going to see the index marks after he has mounted the outer board, it is difficult to find the index marks because they become out of the field of view of the person. As the result, if the measurement is conducted at the dark place, for instance, at the bathing booth, it may happen that the person would mount the outer board at the position offset from the electrodes. This may produce an error in measurement, or in the worst case, the measurement can not be conducted at all.

Furthermore, because the reflection type liquid crystal display unit is designed to need the surrounding light for readily visible display, it is difficult to see such display unit at the dark place.

In addition, the display unit simply indicates the measurement result numerically or graphically, and therefore, it produces no strong impression to the person to be measured. In particular a corpulent person would not have the strong perception that he is corpulent after the measurement.

Finally the prior art apparatus is defective in that it must be disassembled to find even a minor fault such as breakage of a lead wire.

In view of the above the present invention aims at solving the problems in the prior art apparatus, as described above. More particularly an object of the present invention is to provide a living body measuring apparatus with a built-in weight meter that is more effective in that there is no possibility of peeling off a paper bearing the important information so that a person to be measured can always read the information. Another object of the present invention is to provide a living body measuring apparatus with a built-in weight meter in which a person to be measured can easily confirm the position on the apparatus where he mounts, can be given a readily visible display of the measurement result, and can easily find a fault, if any.

SUMMARY OF THE INVENTION

To attain such objects the present invention provides a living body measuring apparatus with a built-in weight meter, comprising: a measuring platform; and electrodes, whereby said measuring platform being constructed in two-layered configuration having inner and outer boards, said electrodes being arranged on said outer board to measure a living body impedance, and said outer board of the measuring platform being formed from a transparent plate. Accordingly a paper bearing the important information may be affixed on the lower surface of the outer board, because it is still visible through the transparent outer board from the upper side. In case where the outer board is a colorless transparent plate the visibility for the information through the outer board becomes more higher.

According to an embodiment of the present invention the measuring platform is constructed in a single-layered configuration having only the outer board that also acts as the inner board. In such case the inner construction of the apparatus becomes visible through the transparent outer board from the outside without any necessity of disassembling the apparatus.

According to another embodiment of the present invention the electrode on the outer board is formed from an electrically conductive transparent coating. Therefore an area of the outer board through which a person can see the opposite side thereof becomes wider. In case where the electrode is formed from an electrically conductive colorless transparent coating said area of the outer board becomes more wider.

According to further embodiment of the present invention the electrode is provided with a projection. Accordingly a person to be measured can correctly place his feet on the electrodes, while confirming the position with feeling of his soles.

According to further embodiment of the present invention the apparatus further comprises a light emitting device mounted in a cavity of the outer board. Therefore the light emitting device emits a light through a display window frame to illuminate the display unit.

According to further embodiment of the present invention the apparatus further comprises a plurality of light emitting devices and a light control unit, whereby said light emitting devices each emitting a light of different color, and said light control unit controlling said light emitting devices to emit a light of different color according to the measurement result. Accordingly a person to be measured can be given a strong impression depending on the measurement result.

BRIEF DESCRIPTION OF THE DRAWINGS

Now the present invention will be described in more detail with reference to a body fat measuring apparatus with a built-in weight meter, i.e., one of the living body measuring apparatus, as shown in the accompanying drawings, in which.

Figure 1A:
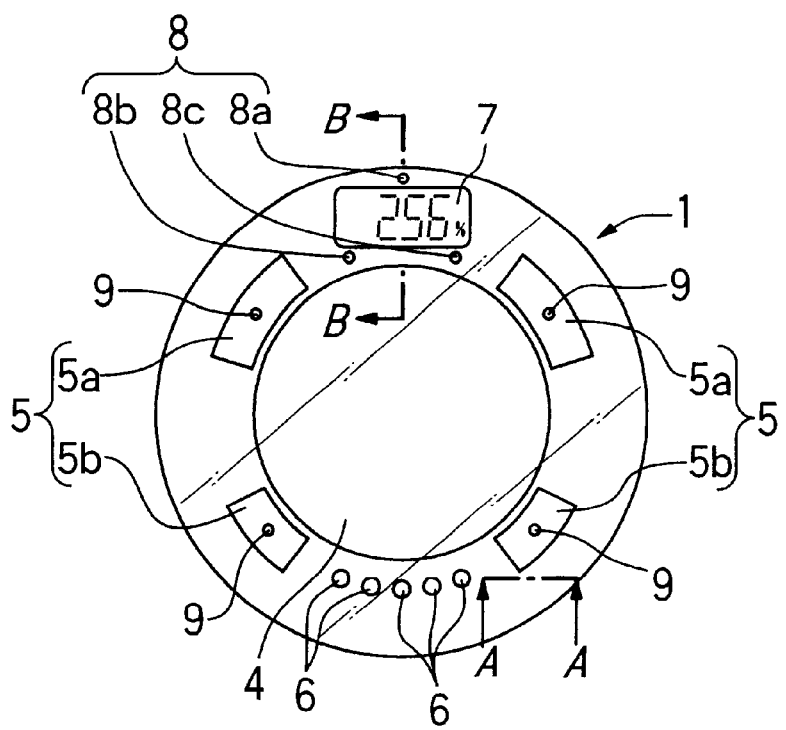
FIG. 1(a) is a plan view of a body fat measuring apparatus with a built-in weight meter according to the present invention.
Figure 1B:
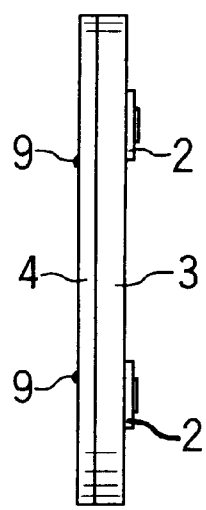
FIG. 1(b) is a side view of the apparatus.
Figure 1C:
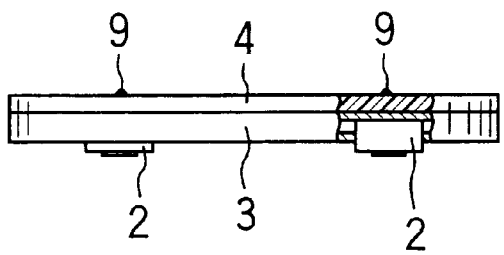
FIG. 1(c) is a front elevation view of the apparatus, partly broken and taken along a line A—A in FIG. 1(a)

DESCRIPTION OF THE PREFERRED EMBODIMENTS:

FIGS. 1(a), 1(b) and 1(c) are an external view illustrating a body fat measuring apparatus with a built-in weight meter according to the present invention. More particularly FIG. 1(a) is a plan view, FIG. 1(b) is a side view, and FIG. 1(c) is a front elevation view, of the body fat measuring apparatus. The body fat measuring apparatus with the built-in weight meter 1 according to the present invention comprises a measuring platform of two-layered configuration having a doughnut type inner board 3 and a circular type colorless transparent outer board 4. The inner board 3 has load sensor units 2 directly mounted thereon, to which the load is exerted directly from a floor. The outer board 4 is configured to directly contact with a person to be measured when he mounts thereon. The outer board 4 includes electrodes 5 for measuring the living body impedance for the person, and input switches 6 for setting the personal condition or parameters used for measurement.

The term "board" as used herein means any flat plate with or without a partial cut out(s), a groove(s) and a projection(s), but including no ribs. The colorless transparent outer board 4 is formed from a colorless transparent methyl methacrylate resin by an injection molding.

The electrodes 5 consists of a pair of current feeding electrodes 5a for forming an electric current path in the living body and of a pair of measurement electrodes 5b for detecting an electric potential induced in the living body. The current feeding electrodes 5a and the measurement electrodes 5b are each formed by a conductive colorless transparent coating directly formed on the outer board 4. The conductive colorless transparent coating is well known in the art and may be formed by a chemical or physical coating of tin oxide or indium oxide.

The current feeding electrodes 5a and the measurement electrodes 5b are each provided with a semi-spherical projection 9 that is formed at the time of resin molding for the outer board 4.

An electronic circuit board 11 mounted in a cavity of the inner board 3 includes a reflection type liquid crystal display unit 7 for displaying the setting condition and the measurement result. The circuit board 11 further includes light emitting devices 8, and a combination of an amplifier, an A/D converter, an arithmetic unit, a memory and a controller unit for processing a detected load signal, as is well known. In addition to the functions as already known in the art, the controller unit provides another function of controlling the light emitting devices. The light emitting devices 8 includes a green light emitting diode 8a, a yellow light emitting diode 8b and a red light emitting diode 8c.

Figure 2:
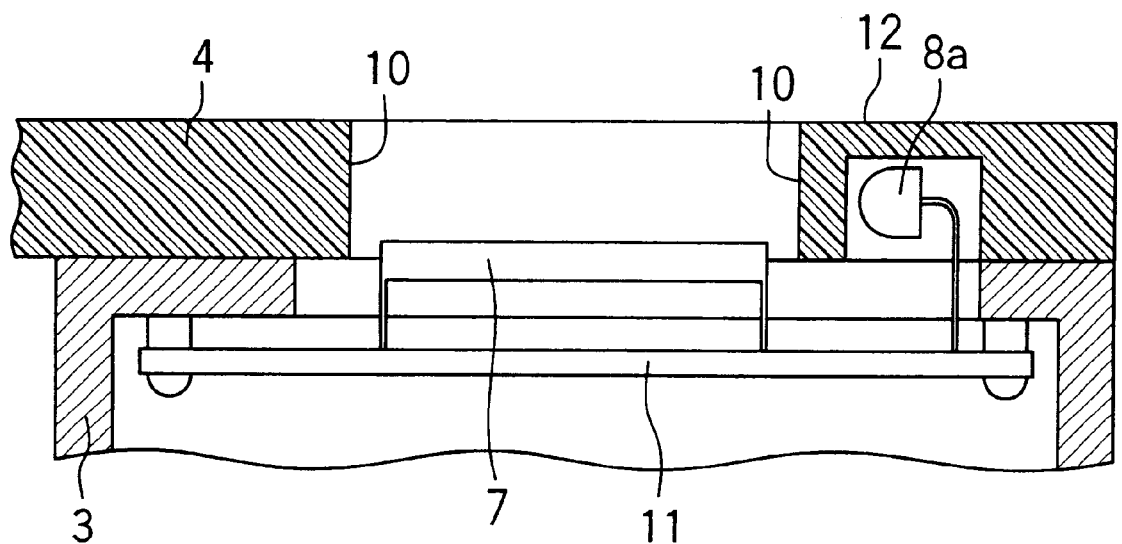
FIG. 2 is an enlarged cross-sectional view of the apparatus, taken along a line B—B in FIG. 1(a).

FIG. 2 is an enlarged cross-sectional view of the apparatus, taken along a line B—B in FIG. 1(a). As can be seen, the electronic circuit board 11 is mounted in the cavity of the inner board 3. The circuit board 11 includes the reflection type liquid crystal display unit 7 mounted thereon at the position surrounded by a surface 10 forming a display window frame in the outer board 4. The circuit board 11 further includes the green light emitting diode 8a positioned in a cavity of the outer board 4. For the sake of clarity, the yellow light emitting diode 8b, the red light emitting diode 8c, the amplifier, A/D converter, arithmetic unit, memory and controller unit are omitted in FIG. 2.

The current feeding electrodes 5a, the measurement electrodes 5b, the load sensor units 2, the input switches 6 and the electronic circuit board 11 are connected to each other by wiring to complete the entire apparatus.

The body fat measuring apparatus with the built-in weight meter 1 is started after setting the personal parameters with the input switches 6 in a manner, as known in the art. The measurement result is displayed on the reflection type liquid crystal display unit 7 in such manner that the body fat rate and the body weight are alternately displayed. At this time, if the body fat rate is within the normal range (for example, 14 to 23% for a male and 17 to 27% for a female), then the controller unit for the light emitting devices acts to turn ON the green light emitting diode 8a. If the body fat rate corresponds to the range for slight corpulence (for example, 25 to less than 30% for a male and 30 to less than 35% for a female) then the controller unit turns ON the yellow light emitting diode 8b. Alternatively if the body fat rate corresponds to the range for corpulence (for example, over 30% for a male and over 35% for a female) then the controller unit turns ON the red light emitting diode 8c.

In the body fat measuring apparatus 1 according to the present invention the outer board 4 is a colorless transparent plate formed from a methyl methacrylate resin so that a person can see the opposite side of the outer board 4. Therefore, it becomes possible to affix a paper bearing the important information such as the caution notice or the description of operation to the lower surface of the outer board 4. This obviates the tendency for a person to be measured to inevitably tread the paper with his soles for measurement, as in before. In addition, even if the person mounts the outer board 4 with his feet as wetted after taking a bath, there is no possibility to wet the paper, thereby preventing the paper from peeling off.

Because the electrodes 5 are formed from the electrical conductive colorless transparent coatings directly on the outer board 4 then an area of the outer board 4 through which the person can see the opposite side thereof becomes wider. Correspondingly an area of the opposite side of the outer board 4 that can be utilized becomes wider. Therefore, the number of, or the size of papers bearing the important information such as the caution notice or the description of operation can be increased.

Because of the projections 9 formed on the electrodes 5 the person to be measured can confirm the correct position with feeling of his soles when he mounts the outer board 4. In addition the person can confirm the correct position even after he has mounted the outer board 4, thereby realizing the precise measurement.

According to the disposition of the light emitting diodes 8a, 8b and 8c within the cavities of the outer board 4 the light emitted by those light emitting diodes is transmitted via the cavities of the outer board 4. The light is then transmitted through the surface 10 forming the display window frame to illuminate the reflection type liquid crystal display unit 7. Therefore the information on the display unit 7 as illuminated by the light is readily visible even when the apparatus is positioned at any dark place. In addition any one of the different colored light emitting diodes 8a, 8b and 8c is turned ON by the controller unit, and therefore, the person to be measured can be given the strong impression about the measurement result. Then the corpulent person can perceives that he is corpulent after the measurement.

Thus far is the description of the preferred embodiment of the present invention, but the present invention may be embodied in any other ways. For example, the outer board 4 may be formed from any colorless transparent material such as glass or polystyrene resin, rather than the methyl methacrylate resin, as described above. In addition any colored, but transparent material may be used with the same advantageous effect, because of the visibility through the outer board 4 still given.

Similarly any electrically conductive transparent coating, rather than the electrically conductive colorless transparent coating, may be used for the electrodes 5 with the same advantageous effect, because the wider area of the outer board 4 through which the person can see the opposite side thereof is still maintained. The electrodes 5 may be modified in such manner that the electrically conductive transparent coating is formed on any other transparent component which is then mounted to the outer board 4, rather than the transparent coating directly formed on the outer board 4, as described above.

Figure 3:
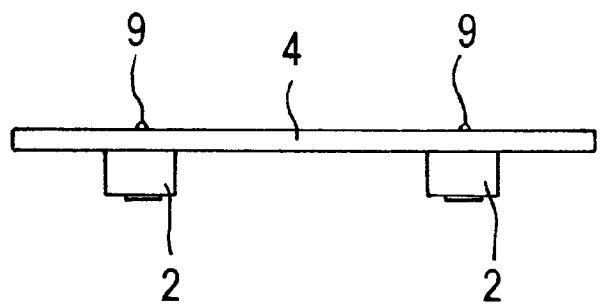
FIG. 3 is a front elevation view of a body fat measuring apparatus with a built-in weight meter according to another embodiment of the present invention.

In an alternative embodiment of the present invention shown in FIG. 3, the inner board 3 may be omitted and the load sensor units 2 may directly be mounted to the transparent outer board 4 to form a single-layered configuration. According to such configuration the inner construction of the apparatus is visible through the transparent outer board from the outside without any necessity of disassembling the apparatus. Therefore, any breakage of lead wires or other defects can readily be found without disassembly of the apparatus.

The projection 9 on the electrode may be any shape of projection such as any letter or any figure, rather than the semi-spherical, as described above. Alternatively a separate projection component may be formed and mounted on the electrode 5, rather than the projection 9 as concurrently molded with the outer board 4.

The colors for the light emitting devices 8 are not limited to red, yellow and green, but any other colors may be used. In addition any other light emitting device may be used, rather than the light emitting diode.

The present invention has been described above with reference to the body fat measuring apparatus with the built-in weight meter, but the present invention is not limited to such embodiment. For example, the present invention may equally apply to a body water measuring apparatus with a built-in weight meter including electrodes for measuring living body impedance, or to a pulsometer with a built-in weight meter.

It is apparent from the foregoing that by making the outer board transparent the paper bearing the caution notice and the description of operation can be affixed to the rear surface of the outer board because they are still visible through the transparent outer board. This obviates the tendency for a person to be measured to inevitably tread the paper with his soles for measurement. Furthermore, if the person mounts the outer board with his feet as wetted after taking a bath, there is no possibility to wet the paper, thereby preventing the paper from peeling off. In addition, by forming the outer board from a colorless transparent plate and forming the electrode from a conductive transparent coating or a conductive colorless transparent coating, higher visibility through the outer board can be attained so that wider area of the outer board can effectively be utilized. This greatly increases the usefulness of the apparatus.

Furthermore, by forming the projection on the electrode, the person to be measured can confirm his position with feeling of his soles when he mounts the outer board. Therefore the person can correctly stands on the electrodes even after he has mounted the outer board, which contributes to realize the precise measurement. By disposing the light emitting devices within the cavities of the outer board the light emitted thereby is transmitted through the surface forming the display window frame to illuminate the reflection type liquid crystal display unit. Therefore the information on the display unit is readily visible even when the apparatus is positioned at any dark place. In addition, because of the controller unit operating any one of the different colored light emitting devices, the person to be measured can be given the strong impression about the measurement result. In particular the corpulent person can perceives that he is corpulent after the measurement. Finally, by forming the single-layered configuration having only the outer board, the inner construction of the apparatus is visible from the outside without any necessity of disassembling. Therefore, any failures or defects in the apparatus can readily be found without disassembly of the apparatus. Those characteristics of the present invention greatly increase the effectiveness of the apparatus.

What is claimed is:

1. A living body measuring apparatus with a built-in weight meter, comprising:

a measuring platform; and a plurality of electrodes, wherein said measuring platform has a two-layered configuration having inner and outer boards, said electrodes being arranged on said outer board to measure a living body impedance, said outer board being formed from a transparent plate; and wherein the area of a top surface of said inner board is smaller than the area of a top surface of said outer board.

2. A living body measuring apparatus with a built-in weight meter according to claim 1 in which said inner board has a doughnut shape.

3. A living body measuring apparatus with a built-in weight meter according to claim 2 in which said outer board of the measuring platform is colorless.

4. A living body measuring apparatus with a built-in weight meter, comprising:

a measuring platform;

a plurality of electrodes; and a load sensor unit, wherein said measuring platform is formed from a transparent outer board in a single-layered configuration, said electrodes being arranged on said measuring platform to measure a living body impedance, said load sensor unit being mounted on said measuring platform, wherein the area of a top surface of said load sensor unit is smaller than the area of a top surface of said measuring platform.

5. A living body measuring apparatus with a built-in weight meter according to any one of claims 1 to 4, wherein said electrodes are formed from an electrically conductive transparent coating.

6. A living body measuring apparatus with a built-in weight meter according to any of claims 1 to 4, wherein said electrodes are formed from an electrically conductive, colorless transparent coating.

7. A living body measuring apparatus with built-in weight meter according to any one of claims 1 to 4, in which said electrodes have a projection.

8. A living body measuring apparatus with a built-in weight meter according to any one of claims 1 to 4, further comprising a light emitting device mounted in a cavity of said outer board.

9. A living body measuring apparatus with a built-in weight meter according to any one of claims 1 to 4, further comprising:

a light emitting device mounted in a cavity of said outer board, said light emitting device including a plurality of light emitting elements each emitting a light of different color; and a light control unit for controlling said light emitting device to emit light of different color according to the measurement results.

* * * * *

(12) EX PARTE REEXAMINATION CERTIFICATE (5901st)
United States Patent
Serizawa et al.

(10) Number: US 6,532,385 C1
(45) Certificate Issued: Sep. 25, 2007

(54) LIVING BODY MEASURING APPARATUS WITH A BUILT-IN WEIGHT METER

(75) Inventors: Takashi Serizawa, Tokyo (JP); Takeshi Iijima, Tokyo (JP)

(73) Assignee: Tanita Corporation, Tokyo (JP)

Reexamination Request:
No. 90/006,875, Nov. 25, 2003

Reexamination Certificate for:
Patent No.: 6,532,385
Issued: Mar. 11, 2003
Appl. No.: 09/776,719
Filed: Feb. 6, 2001

(30) Foreign Application Priority Data

Feb. 16, 2000 (JP) ......................................... 2000-037570

(51) Int. Cl.
*A61B 5/05* (2006.01)
*A61B 5/103* (2006.01)
*A61B 5/117* (2006.01)

(52) U.S. Cl. ........................................ 600/547; 600/595
(58) Field of Classification Search .................... None
See application file for complete search history.

(56) References Cited

U.S. PATENT DOCUMENTS

| | | | |
|---|---|---|---|
| 4,278,875 A | 7/1981 | Bain | |
| 4,699,804 A | 10/1987 | Miyata et al. | |
| 5,324,374 A | 6/1994 | Harmand et al. | |
| 5,415,176 A | 5/1995 | Sato et al. | |
| 5,505,200 A | 4/1996 | Takaki | |
| 5,575,292 A | 11/1996 | Brown et al. | |
| 5,579,782 A | 12/1996 | Masuo | |
| 5,886,302 A | 3/1999 | Germanton et al. | |
| 5,900,275 A | 5/1999 | Cronin et al. | |
| 5,955,705 A * | 9/1999 | Germanton | 177/126 |
| 5,968,416 A | 10/1999 | Smith et al. | |
| 6,221,520 B1 * | 4/2001 | Takaki et al. | |
| D444,403 S | 7/2001 | Joss et al. | |
| 6,292,690 B1 | 9/2001 | Petrucelli et al. | |
| 6,532,385 B2 | 3/2003 | Serizawa et al. | |
| 6,748,264 B2 | 6/2004 | Chai | |

FOREIGN PATENT DOCUMENTS

| | | |
|---|---|---|
| CA | 2262924 | 3/1999 |
| CN | 1235545 C | 1/2006 |
| DE | 41 23 042 A1 | 4/1992 |
| DE | 196 39 095 A1 | 3/1998 |
| DE | 201 22 592.1 | 6/2006 |
| EP | 1 078 733 A1 | 2/2001 |
| EP | 1 125 550 A1 | 8/2001 |
| EP | 1 466 556 A1 | 10/2004 |
| EP | 1 125 550 B1 | 4/2005 |
| EP | 1 665 982 A1 | 6/2006 |

(Continued)

OTHER PUBLICATIONS

Copy of photograph of apparatus with descriptive paragraph and specifications for "BF576 The Sophisticated Glass Model of 'Body Fat Monitor/Scales'".

(Continued)

*Primary Examiner*—Beverly M. Flanagan

(57) ABSTRACT

Disclosed is a living body measuring apparatus with a built-in weight meter, comprising: a measuring platform; and electrodes, whereby said measuring platform being constructed in two-layered configuration having inner and outer boards, said electrodes being arranged on said outer board to measure a living body impedance, and said outer board of the measuring platform being formed from a transparent plate. Therefore a paper bearing the caution notice or the description of operation can be affixed to the lower surface of the outer board because they are still visible through the transparent outer board. This obviates the tendency for a person to be measured to inevitably tread the paper with his soles for measurement. Furthermore, if the person mounts the outer board with his feet as wetted after taking a bath, there is no possibility to wet the paper, thereby preventing the paper from peeling off.

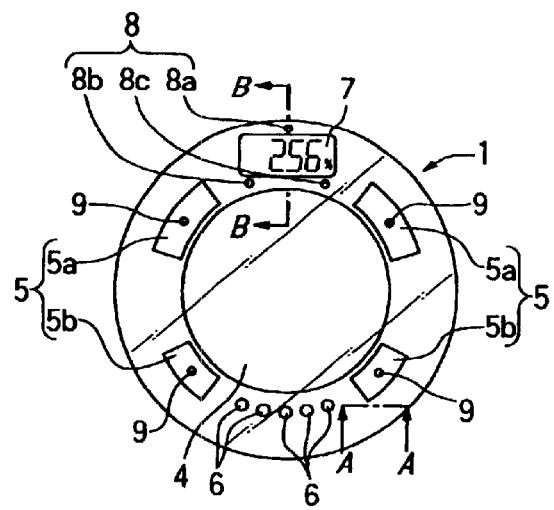

FOREIGN PATENT DOCUMENTS

| | | |
|---|---|---|
| JP | 59-127136 | 8/1984 |
| JP | 62-169023 | 7/1987 |
| JP | 63-315916 | 12/1988 |
| JP | 08-244186 | 9/1996 |
| JP | 9-33327 | 2/1997 |
| JP | 09-033327 | 2/1997 |
| JP | 10-096706 | 4/1998 |
| JP | 10-179536 | 7/1998 |
| JP | 2001-228013 | 8/2001 |
| WO | WO 98/13674 | 4/1998 |

OTHER PUBLICATIONS

Copy of photograph of apparatus and packaging for "BaByliss High Tech Paris, Bodyslim Impedancemetre Bodyfat Control, ITO Technologies".

Copy of photograph of apparatus with descriptive paragraph and specifications for "Soehnle Body Balance, Body Balance Pacific, Art–Nr.: 63627, EAN–Code: 4006501 63627 0" and "Soehnle Body Balance, Body Balance Sydney, Art–Nr.: 63626, EAN–Code: 4006501 63626 3".

Copy of photograph of apparatus with descriptive paragraph and specifications for "Soehnle Body Balance, Body Balance, Art–Nr.: 63571, EAN–Code: 4006501 63571 6" and "Soehnle Body Balance, Body Balance Paris, Art–Nr.: 64100, EAN–Code: 4006501 64100 7" and "Soehnle Body Balance, Body Balance Barcelona, Art–Nr.: 64101, EAN–Code: 4006501 64101 4".

Copy of photograph of apparatus and packaging for "BaByliss High Tech Paris, Bodyslim Weight and Body Fat Control".

Copy of photograph of apparatus with descriptive paragraph and specifications for "Perfect Control Measurement of the Body Fat, EAN Nos. 401632408091, 4016324085063, and 4016324085070".

Copy of photograph of apparatus "Thinner".

Copy of photograph of apparatus "Korona 2003, Innovation in Technique and Design".

Copy of photograph of apparatus with descriptive paragraph and specifications for "Soehnle Orion, 7310 00" and "Soehnle xi 7402 00".

1999 Soehnle Italia Catalog.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–3 is confirmed.

Claim 4 is cancelled.

Claims 5–9 are determined to be patentable as amended.

New claims 10–20 are added and determined to be patentable.

5. A living body measuring apparatus with a built-in weight meter according to any one of claims 1 to [4]*3*, wherein said electrodes are formed from an electrically conductive transparent coating.

6. A living body measuring apparatus with a built-in weight meter according to any of claims 1 to [4]*3*, wherein said electrodes are formed from an electrically conductive, colorless transparent coating.

7. A living body measuring apparatus with built-in weight meter according to any one of claims 1 to [4]*3*, in which said electrodes have a projection.

8. A living body measuring apparatus with a built-in weight meter according to any one of claims 1 to [4]*3*, further comprising a light emitting device mounted in a cavity of said outer board.

9. A living body measuring apparatus with a built-in weight meter according to any one of claims 1 to [4]*3*, further comprising:

a light emitting device mounted in a cavity of said outer board, said light emitting device including a plurality of light emitting elements each emitting a light of different color;

and a light control unit for controlling said light emitting device to emit light of differerent color according to the measurement results.

*10. A living body measuring apparatus with a built-in weight meter, comprising:*

*a measuring platform;*

*a plurality of electrodes; and*

*load sensor unit;*

*wherein said measuring platform is formed from a transparent outer board in a single-layered configuration, said electrodes being arranged on said measuring platform to measure a living body impedance, said load sensor unit being mounted on said measuring platform; and*

*wherein the area of a top surface of said load sensor unit is smaller than the area of a top surface of said measuring platform;*

*the apparatus further comprising a light emitting device mounted in a cavity of said outer board.*

*11. A living body measuring apparatus with a built-in weight meter, comprising:*

*a measuring platform;*

*a plurality of electrodes; and*

*a load sensor unit;*

*wherein said measuring platform is formed from a transparent outer board in a single-layered configuration, said electrodes being arranged on said measuring platform to measure a living body impedance, said load sensor unit being mounted on said measuring platform; and*

*wherein the area of a top surface of said load sensor unit is smaller than the area of a top surface of said measuring platform;*

*the apparatus further comprising a light emitting device mounted in a cavity of said outer board, said light emitting device including a plurality of light emitting elements each emitting a light of different color, and a light control unit for controlling said light emitting device to emit light of different color according to the measurement results.*

*12. A living body measurement apparatus with a built-in weight meter according to claim 1, further comprising a plurality of load sensor units,*

*wherein an electronic circuit board is mounted on said inner board, and*

*wherein at least one of said load sensor units is physically connected to said inner board.*

*13. A living body measurement apparatus with a built-in weight meter according to claim 12, in which said load sensor unit is directly mounted on said inner board.*

*14. A living body measurement apparatus with a built-in weight meter according to claims 12 or 13 in which said electrode and said load sensor unit are each arranged on opposite sides of said outer board.*

*15. A living body measurement apparatus with a built-in weight meter according to claims 12 or 13 in which said outer board is colorless.*

*16. A living body measurement apparatus with a built-in weight meter according to claims 12 or 13 in which said electrodes comprise an electrically conductive transparent coating.*

*17. A living body measurement apparatus with a built-in weight meter according to claims 12 or 13 in which said electrodes comprise an electrically conductive, colorless transparent coating.*

*18. A living body measurement apparatus with a built-in weight meter according to claim 17 in which said electrodes have a projection.*

*19. A living body measurement apparatus with a built-weight meter according to claims 12 or 13, further comprising a light emitting device mounted in a cavity of said outer board.*

*20. A living body measurement apparatus with a built-in weight meter according to claims 12 or 13, further comprising:*

*a light emitting device mounted in a cavity of said outer board, said light emitting device including a plurality of light emitting electrodes each emitting a light of a different color; and*

*a light control unit for controlling said light emitting device to emit light of a different color according to the measuring results.*

* * * * *